United States Patent [19]

Geluk

[11] Patent Number: 4,996,701
[45] Date of Patent: * Feb. 26, 1991

[54] METHOD AND DEVICE FOR SLIT RADIOGRAPHY

[75] Inventor: Ronald J. Geluk, Nootdorp, Netherlands

[73] Assignee: B. V. Optische Industrie "De Oude Delft", Delft, Netherlands

[*] Notice: The portion of the term of this patent subsequent to Apr. 10, 2007 has been disclaimed.

[21] Appl. No.: 417,567

[22] Filed: Oct. 5, 1989

Related U.S. Application Data

[63] Continuation of Ser. No. 63,176, Jun. 17, 1987.

[30] Foreign Application Priority Data

Jun. 26, 1986 [NL] Netherlands ............ 8601678

[51] Int. Cl.⁵ .................................................. G21K 5/10
[52] U.S. Cl. ..................................... 378/146; 378/145; 378/149
[58] Field of Search ............... 378/145, 146, 147, 150, 378/151, 152, 153, 156, 157, 158, 160

[56] References Cited

U.S. PATENT DOCUMENTS

| 4,675,893 | 6/1987 | Duinker et al. | 378/146 |
| 4,679,221 | 7/1987 | O'Brien et al. | 378/148 |
| 4,916,723 | 4/1990 | Geluk | 378/146 |

Primary Examiner—Carolyn E. Fields
Assistant Examiner—David P. Porta
Attorney, Agent, or Firm—Louis E. Marn

[57] ABSTRACT

In a method for slit radiography a fan-shaped X-ray beam scans a body to form an X-ray shadow image. The fan-shaped beam is formed by a number of sectors situated next to each other. For each sector the transmitted X-ray radiation is controlled instantaneously during a scan by means of controllable beam sector modulators. The X-ray radiation is cyclically modulated in a predetermined manner for all the sectors taken together. The controllable beam sector modulators are individually controlled to select cyclically and in synchronism with the predetermined cyclic modulation a part of the X-ray radiation for each sector.

40 Claims, 6 Drawing Sheets

METHOD AND DEVICE FOR SLIT RADIOGRAPHY

This is a continuation, of application Ser. No. 07/063,176, filed June 17, 1987.

The invention relates to a method for slit radiography in which use is made of an X-ray source and a slit diaphragm placed in front of the X-ray source to form a fan-shaped X-ray beam with which a body to be investigated is at least partially scanned to form an X-ray shadow image on an X-ray detector placed behind the body, which fan-shaped X-ray beam is formed by a number of sectors situated next to each other, and in which the transmitted X-ray radiation is controlled instantaneously for each sector during the scanning movement by means of controllable beam sector modulators acting in conjunction with the slit diaphragm. In addition, the invention relates to a device for applying the method.

Such a method and such a device are known from Dutch patent application No. 8400845. According to the technique known from Dutch patent application No. 8400845, to control the quantity of X-ray radiation transmitted through the slit diaphragm at each point of time, use is made of attenuation elements which are placed near or in the slit of the slit diaphragm and act as beam sector modulators, which are each able to control a sector of the fan-shaped X-ray beam, and which, depending on the attenuation occurring in the associated sector and caused by the body to be investigated are controlled in a manner such that the attenuation elements extend to a lesser or greater degree into the X-ray beam. If the attenuation caused by the irradiated body in a certain sector and at a certain instant is large, the attenuation element associated with said sector is moved completely or largely out of the X-ray beam. On the other hand, if the attenuation caused by the body in a certain sector at a certain instant is low, then the associated attenuation element is brought further into the X-ray beam.

The advantage of this technique is that equalized X-ray photographs can be obtained therewith, i.e. X-ray photographs which have a good contrast both in the light parts and in the dark parts. If, therefore, a photograph is made in this manner, for example, of the upper part of a patient's body, the radiologist can find sufficient information in the same photograph relating to both the chest and the abdomen of the patient, whereas previously two different photographs were necessary to obtain the same information.

The known technique has the drawback that at the instant when the soft tissues of the patient are irradiated, the X-ray radiation still transmitted in the sector concerned is relatively hard, whereas soft radiation is adequate for the soft tissues and is also to be preferred.

The object of the invention is, therefore, to simplify and to improve the known technique and in general to make available an effective method and equipment for producing equalized X-ray photographs.

For this purpose, according to the invention, a method of the type described is characterized in that the X-ray radiation is cyclically modulated in a predetermined manner for all the sectors taken together and that the controllable beam sector modulators are individually controlled in order to select cyclically a part of the X-ray radiation for each sector, which cyclic selection is synchronized with the predetermined cyclic modulation of the X-ray radiation.

A device for slit radiography, comprising an X-ray source, a slit-type diaphragm, placed in front of the X-ray source, which forms a fan-shaped X-ray beam with which a body to be investigated can be scanned at least partially to form an X-ray shadow image of the scanned part of the body on an X-ray detector placed behind the body, a control signal generator which, during operation, provides a signal representing the transmission of the body for each sector of the X-ray beam to control means, controllable beam sector modulators which act together with the slit diaphragm and which, under the control of signals from the control means, are able to influence the X-ray beam for each sector, is characterized, according to the invention, by modulation means for providing an X-ray beam modulated in a predetermined cyclical manner.

The invention will be described below in more detail with reference to the accompanying drawing.

Figure 2:
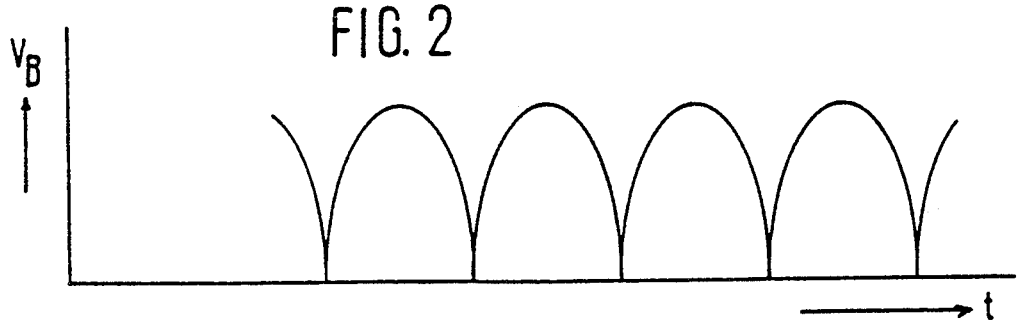
FIG. 2 shows diagrammatically an example of a manner in which an X-ray beam can be provided with a fixed modulation according to the invention.
Figure 3:
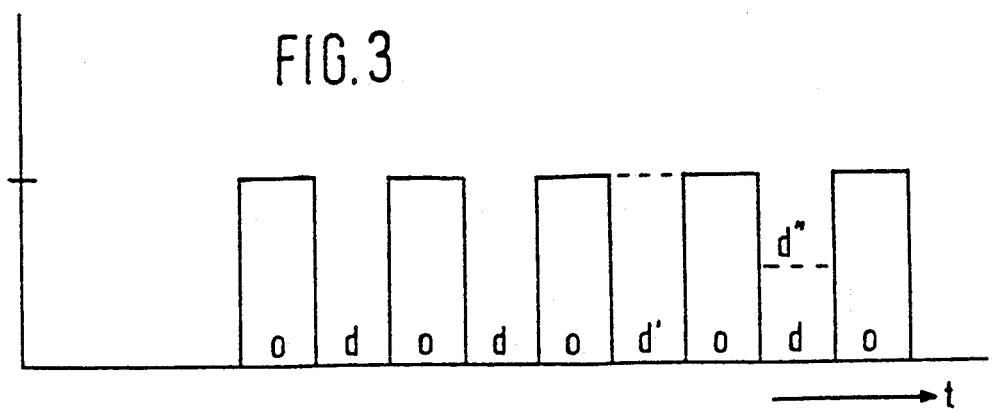
FIG. 3 shows a control diagram of the attenuation elements.
Figure 16:
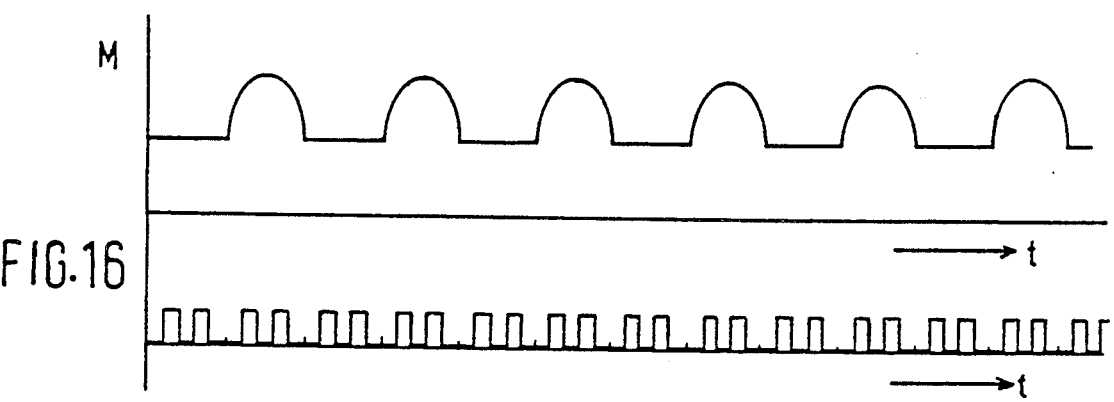
Figure 17:
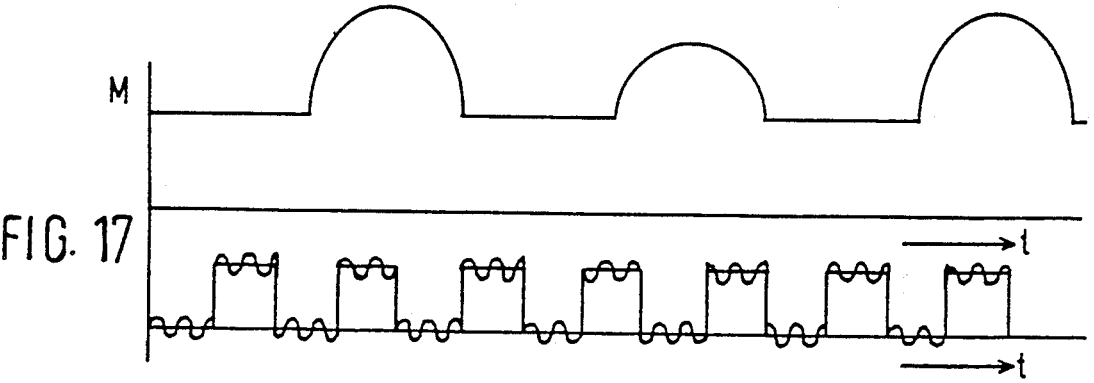

FIGS. 10 to 15 incl. show various embodiments of mechanical modulation means to be used in the invention;

FIGS. 16 and 17 illustrate a few more variations of FIGS. 2 and 3.

Figure 1:
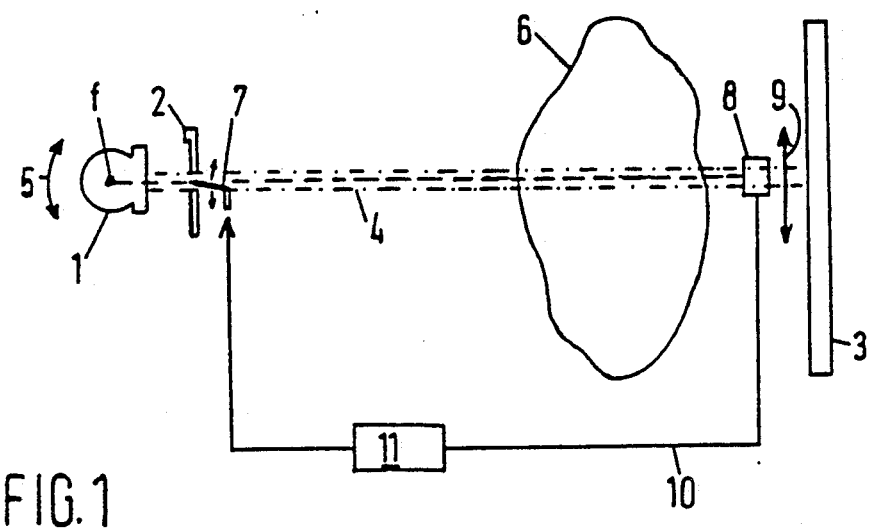
FIG. 1 shows diagrammatically an example of a device for slit radiography.

FIG. 1 shows diagrammatically an example of a device for slit radiography, comprising an X-ray source 1, a slit diaphragm 2 placed in front of the X-ray source, and an X-ray screen 3. The slit diaphragm 2 transmits a fan-shaped X-ray beam 4 having a relatively low thickness. In operation, the X-ray source and/or the slit diaphragm are moved in a manner such that the X-ray beam 4 scans the X-ray detector 3. For this purpose, for example, the X-ray source may be swung together with the slit diaphragm about an axis extending transversely to the plane of the drawing through the X-ray focus f as indicated by an arrow 5. If a body 6 to be irradiated is situated between the X-ray source and the X-ray detector, an X-ray photograph can be taken in this manner of (a part of) the body 6. Attention is drawn to the fact that, instead of a stationary X-ray detector, a strip-like X-ray detector may also be used in the manner described in Dutch patent application No. 8303156.

In order to be able to influence the amount of X-ray radiation transmitted through the slit diaphragm per sector of the fan-shaped X-ray beam to take an equalized X-ray photograph, controllable attenuation elements 7 are present which act in conjunction with the slit diaphragm and which act as beam sector modulators. The attenuation elements may be constructed in various manners, such as described, for example, in Dutch patent application No. 8400845. In the example shown in FIG. 1, the attenuation elements are tongue-shaped and the free ends of the tongues can be swung to a greater or lesser extent into the X-ray beam under the influence of suitable control signals. The attenuation elements may, however, also be of the slider type as also described in Dutch patent application No. 8400845.

To generate the control signals needed for the attenuation elements, there is a detector present which is situated beyond the body 6 to be irradiated and which detects the radiation transmitted by the body 6 for each sector of the X-ray beam and delivers corresponding electrical signals. The detector may consist of a row of light detectors which are situated behind the X-ray screen at the height of the incident beam and which detect the amount of light generated by the X-ray screen 3 under the influence of the incident X-ray radiation. It is also possible to detect the X-ray radiation transmitted through the X-ray screen 3. The detector may also be situated in front of the X-ray screen and may then consist for example of an oblong dosimeter such as described, for example, in the applicant's earlier Dutch patent applications No. 8503152 and 8503153.

Such a dosimeter is diagrammatically indicated in FIG. 1 at 8 and is moved synchronously together with the scanning X-ray beam as is indicated by an arrow 9. The signals originating from the dosimeter are fed via an electrical conductor 10 to a control circuit 11 which forms the control signals for the attenuation elements.

In the technique described hitherto, a constant spectrum and a constant intensity of the X-ray beam delivered by the X-ray source is assumed before it is influenced by the attenuation elements.

According to the invention, on the other hand, the radiation flux and/or the hardness of the X-ray beam is modulated in a predetermined fixed manner, while a sectorwise controlling of the X-ray beam also takes place in addition by means of the attenuation elements. As will emerge below, it is possible, in this manner, for a simpler control of the attenuation elements to be sufficient, while, in certain embodiments of the invention, the high-voltage supply of the X-ray tube can also be simpler.

The predetermined fixed influencing of the X-ray beam can be achieved in various manners.

According to a first exemplary embodiment of the invention, the high voltage of the X-ray tube is modulated with a fixed ripple voltage. If a ripple voltage with the mains frequency (50 Hz or 60 Hz) is used, the high-voltage supply for the X-ray tube can be relatively cheap because no measures are then necessary to eliminate the ripple in the supply voltage which is always present and is caused by the mains frequency.

FIG. 2 shows an example of a modulated supply voltage $V_B$ for the X-ray tube. Such a voltage can be obtained in a simple manner by full-wave rectification of a normal sinusoidal alternating voltage. The value of the supply voltage of the X-ray tube determines the hardness of the X-ray radiation and, in particular, in such a manner that the hardness of the X-ray radiation increases with a higher value of $V_B$. An X-ray tube energized with a supply voltage of the type shown, therefore, delivers an X-ray beam whose hardness increases cyclically in synchronism with the supply voltage from a minimum value to a maximum value and then again decreases to the minimum value.

In combination with the varying supply voltage, the position of the attenuation elements is controlled in a manner such that each attenuation element is in the open position during the intervals o when the tube voltage is low, while in the intervening intervals d, the attenuation elements are in principle in the closed position so that the X-ray beam is essentially intercepted in said intervals.

FIG. 3 illustrates the variation, achieved in this manner, in the position of one of the attenuation elements between the fully closed position and the fully open position. The other attenuation elements are controlled in synchronism in the same manner. The attenuation elements, therefore, transmit in principle only relatively soft radiation.

In order to obtain the desired sectorwise influencing of the X-ray beam as a function of the radiation transmitted in the sector concerned through the irradiated body, the intensity of the radiation transmitted by the irradiated body is measured during the intervals o, for example by means of the dosimeter 8, in each sector. For those sectors in which a predetermined minimum intensity is not reached, the closing of the attenuation elements concerned is prevented during the subsequent interval. In this manner, harder radiation is transmitted in those sectors in which parts of the irradiated body which are less transparent to X-ray radiation are situated. In FIG. 3, this is indicated diagrammatically by a broken line for the interval d'. If the predetermined minimum radiation intensity is again reached or exceeded in a certain sector during a subsequent interval o, the associated attenuation element is again closed in the interval d subsequent thereto.

Since the scanning X-ray beam has a certain thickness which may be, for example, approximately 4 cm at the position of the X-ray detector, the brightness of each image point of the X-ray photograph is determined by integration of the instantaneous brightness values which occur during the passage of the scanning beam over the image point concerned. As a result thereof, excessively sharp light-dark transitions are avoided in the final X-ray photograph in the scanning direction. A contribution is also made to this by the fact that in practice the opening and closing of the attenuation elements requires some time.

This control of the attenuation elements is very simple since the latter only have to be brought to two discrete positions (fully open or fully closed) and since it is only necessary to detect whether the radiation transmitted by the irradiated body exceeds or does not exceed a predetermined value of intensity.

The manner described in the foregoing of controlling the attenuation elements may, if desired, be refined by making use of more than two possible discrete positions of the attenuation elements. Thus, for example, a half-closed intermediate position may be defined in which an attenuation element is brought if the value of intensity of the radiation transmitted by the irradiated body in the associated sector lies between two predetermined values. Such an intermediate position is indicated diagrammatically with a broken line at d". It is also possible to use several intermediate positions or even a continuous variation of the position.

The manner described in the foregoing of controlling the attenuation elements could be termed an amplitude control because the attenuation elements are brought to one of a number of possible discrete positions during predetermined time intervals.

As an alternative it is possible to use a phase control in which each attenuation element alternately opens and closes, but in which the point of time at which this takes place may be displaced with respect to the modulated high voltage of the X-ray tube or the X-ray beam modulated in a fixed way in another manner.

Figure 4:
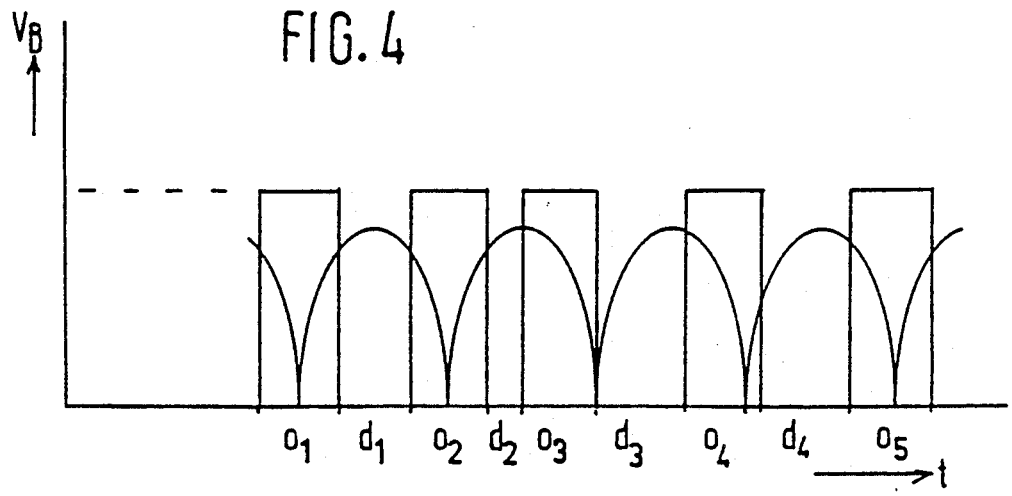
FIGS. 4, 5 and 6 show variations of FIG. 3.

FIG. 4 illustrates the principle of the phase control system. FIG. 4 shows, in the same manner as FIG. 2, the fixed modulation of the X-ray beam obtained by modulation of the high voltage of the X-ray tube. In addition, in FIG. 4 intervals are indicated by way of example for a single attenuation element during which the attenuation element is completely opened or completely closed.

During the intervals $o_1$ and $o_2$, the attenuation element is opened during intervals in which the high-voltage of the X-ray tube is relatively low, just as in the manner of control previously described. If the radiation transmitted by the irradiated body in the sector associated with the attenuation element concerned has an intensity below a predetermined value during the second "open" interval $o_2$, the beginning of the third "open" interval $o_3$ is advanced by a predetermined time, as shown in FIG. 4. In the sector of the X-ray beam concerned, the body to be irradiated received harder X-ray radiation as a result of this. In the situation shown in FIG. 4, both the beginning and the end of the interval $o_3$ have been advanced, and the length of the interval is unchanged. In order to be able to determine whether the subsequent interval should also be advanced, the measurement of the radiation transmitted by the irradiated body in the sector of the X-ray beam concerned should also take place during the advanced "open" interval. To do this, the procedure may be such that, if the intensity of the radiation transmitted by the irradiated body in said sector during the advanced interval does not exceed a predetermined maximum value, the subsequent interval is also advanced in the same manner, as indicated in FIG. 4 for the interval $o_4$.

Figure 5:
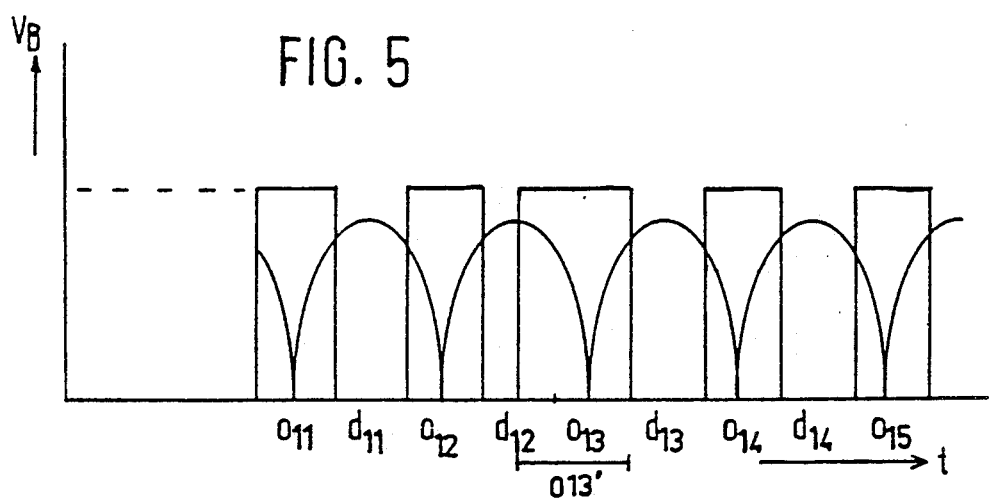

As an alternative, it is also possible to advance only the starting point of an "open" interval by a predetermined time as soon as the radiation transmitted by the body in the associated sector of the X-ray beam fails to reach the predetermined value of intensity in a preceding "open" interval, but to leave the end point of the interval concerned unchanged. As a result the interval, therefore, becomes longer but still contains the complete original "open" interval as well. All this is shown in FIG. 5. In FIG. 5 the starting point of interval $o_{13}$ has been advanced so that an extended open interval $o_{13}'$ is produced, during which harder radiation is transmitted in addition to the relatively soft radiation transmitted by the attenuation element concerned in the preceding intervals. The extended interval contains also the complete unextended interval $o_{13}$. The measurement of the intensity of the radiation transmitted through the irradiated body in the sector concerned can still, therefore, take place in the "original" interval $o_{13}$. If the measured value of intensity then again fails to reach the predetermined threshold value, the starting point of the subsequent "open" interval is also advanced.

The simplest form of the phase control described could be based on only two different positions of the "open" intervals with respect to the curve representing the fixed modulation of the X-ray beam.

Figure 6:
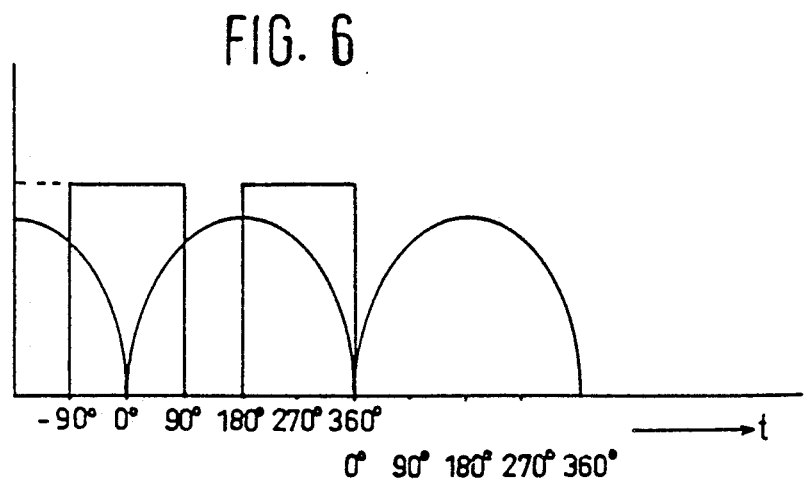

If, as shown in FIG. 6, a peak of the modulation curve is regarded in each case as a complete cycle which contains a phase trajectory of 360°, the control circuit could, for example, be constructed in a manner such that the "open" interval of an attenuation element extends either from −90° (=270°) to +90°, or from 180° to 360° (by analogy with FIG. 4), or such that the "open" interval always ends at 90° but the starting point is either at −90° (=270°) or at 180° (with reference to FIG. 5). It is obviously also possible to choose a different position for the advanced "open" interval.

A refined phase control system may be obtained by choosing a number of different discrete threshold values of the radiation intensity measured behind the body irradiated and, consequently, corresponding fixed phase trajectories for the "open" intervals of the attenuation elements.

The most precise control is obtained if the position of at least the starting point of the open intervals can be varied continuously as a direct function of the instantaneous value of the measured intensity of the radiation transmitted by the irradiated body.

Attention is drawn to the fact that, as follows directly from FIGS. 4 to 6 incl., phase control can be achieved with the same effect by delaying the "open" interval, or at least the endpoint thereof. Use is made of this principle in one embodiment of the invention to be described in yet further detail below.

In the Dutch patent application No. 8400845 mentioned earlier, attenuation elements acting as beam sector modulators are described which are tongue-shaped or constructed as slides and which can take up any position between a position exposing the slit of the slit diaphragm completely and covering the slit completely under influence of the control signals. Such attenuation elements may also readily be used within the scope of the present invention. However, because the attenuation elements are opened and closed at a constant frequency in the phase control system described above, only the point of time of opening and/or closing being varied, use may be made of a continuously rotating spindle provided with attenuation elements.

Figure 7:
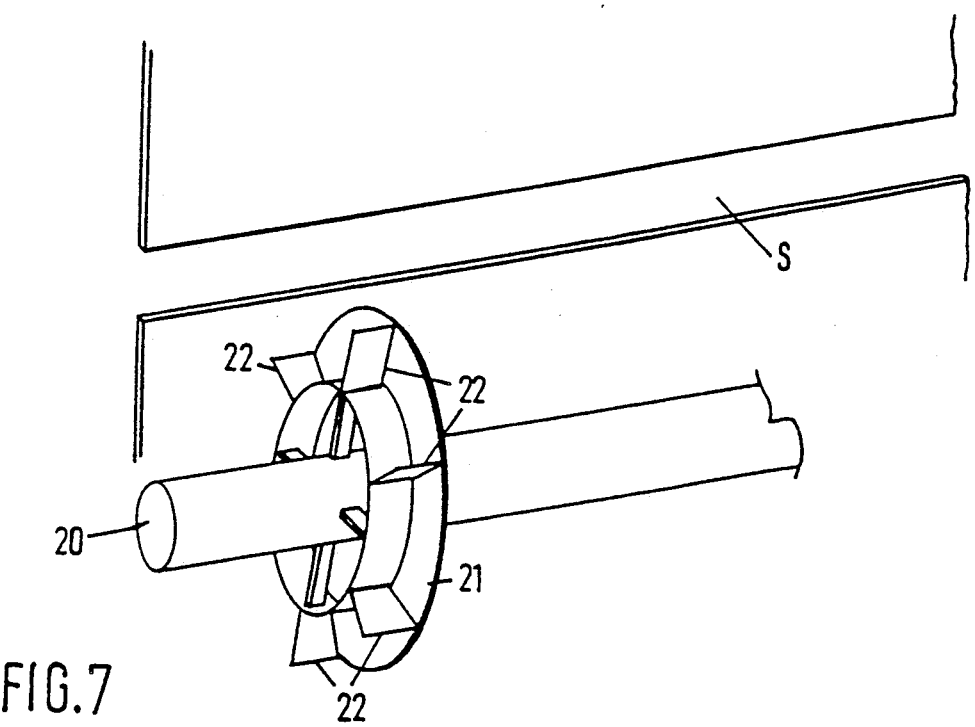
FIGS. 7 and 8 illustrate diagrammatically a detail of a device according to the invention.
Figure 8:
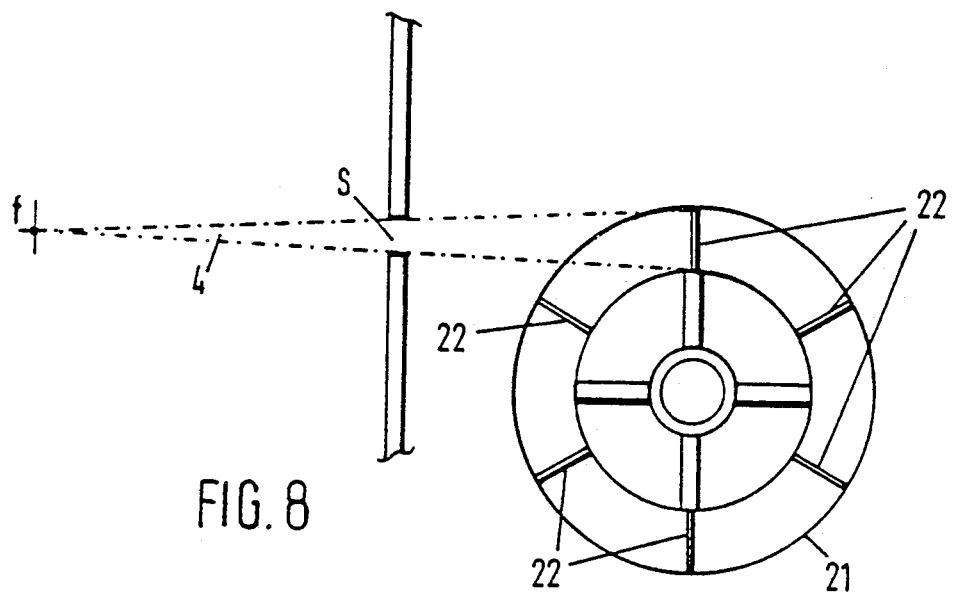

All this is shown diagrammatically in FIG. 7. FIG. 7 shows the slit S of the slit diaphragm of a slit radiography device. In front of the slit diaphragm there is placed a spindle 20 which can be made to rotate by means not shown. On the spindle 20 there are placed next to each other wheels of a blade type, only one of which, indicated by 21, is shown. The blade wheels together occupy the entire length of the slit S. The blades 22 of the blade wheels consist of material which attenuates or blocks X-ray radiation and extend to a distance from the spindle 20 placed somewhat higher or lower than the slit S, such that during the rotation of the spindle each blade in each case covers the section of the slit S situated opposite the blade wheel for a short time, as can be seen in FIG. 8. The dimensions of the blades, distribution of the blades over the circumference of the blade wheel and the number of blades are chosen in a manner such that on rotating the spindle at a fixed rotary speed matched to the frequency or the fixed modulation of the X-ray beam 4, the slit is cyclically covered or exposed by the blades.

In order to be able to implement the required phase control, it must be possible to vary the position of each blade wheel separately with respect to the spindle 20 at least temporarily. For this purpose, the blade wheels are mounted in a slipping or sprung manner on the spindle and each blade wheel is provided with an electrically energizable brake. When the brake of a blade wheel is energized, the angular position of said blade wheel changes with respect to the spindle 20 so that the next blade begins to intercept the X-ray beam later and the phase of the open intervals changes with respect to the fixed modulation of the X-ray beam.

Figure 9:
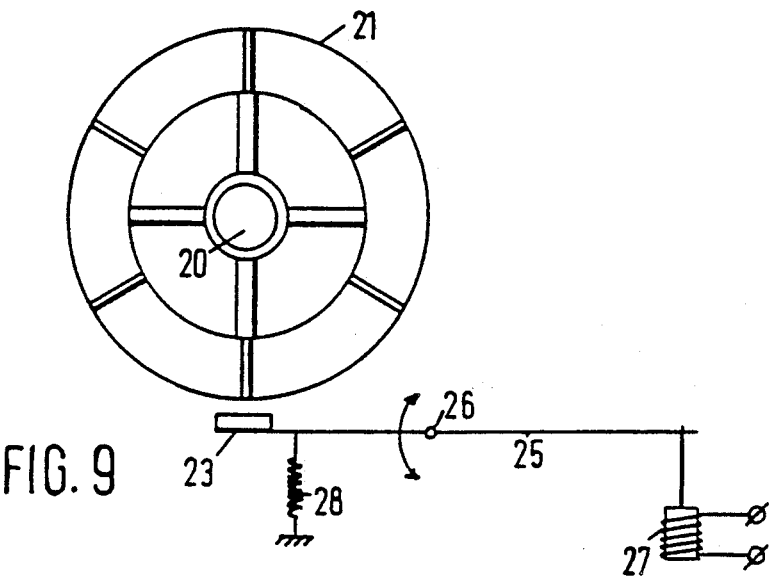
FIG. 9 shows diagrammatically another detail of a device according to the invention.

An example of a brake for a blade wheel is shown diagrammatically in FIG. 9. The brake comprises a small brake block 23 which is placed at the end of a lever 25 having a pivot point 26 and which is situated near the circumference of the blade wheel 21. The other end of the lever is joined to the mobile core of a coil 27 which can be energized and to which the control signals are fed. The brake is held in the non-blocking position by a spring 28 in the absence of control signals. If the blade wheel is mounted in a slipping manner on the spindle 20 a brief energizing of the brake causes a permanent change in position and, consequently, a permanent phase shift. A phase shift brought about in this manner can be cancelled again by energizing the brake again until the change in position of the blade wheel has become equal to the angular distance between two blades.

Figure 10:
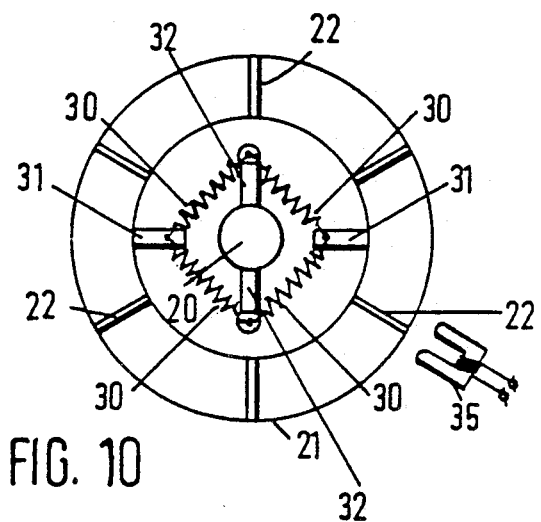
FIG. 10 shows a variation of FIG. 9.

In the embodiment of FIG. 10, the blade wheel is provided with four springs 30 which each extend between a spoke 31 of the blade wheel and a projection 32 of the spindle 20. In this case the brake has to remain energized as long as the phase change has to be maintained. After termination of the brake energizing, the blade wheel automatically assumes the original position again as a result of the action of the springs 30.

A blade wheel with attenuation elements can be manufactured in various manners. A possibility is to construct the blade wheel solidly in a suitable plastic in which the blades forming the attenuation elements are embedded.

An important advantage of using rotating attenuation elements is that a high frequency can be chosen for exposing or covering the slit S, with a corresponding high fixed modulation frequency of the X-ray beam, which ensures a better uniformity of the exposure of the X-ray detector.

The position of the blade wheels can also be controlled in a manner other than that shown in FIG. 9. FIG. 10 shows, by way of example, an eddy-current brake 35 interacting with a blade wheel.

In the foregoing it has already been indicated that the fixed modulation of the X-ray beam delivered by the X-ray source can be brought about by cyclically varying the high voltage of the X-ray tube. This produces a varying hardness of the X-ray beam. It is also possible to modulate the current flowing through the X-ray tube, as a result of which a varying intensity of the X-ray beam is obtained.

As an alternative, the fixed modulation can be brought about by means of mechanical means. Such mechanical means should comprise one or more elements which cyclically cover the slit of the slit diaphragm. A first embodiment of such mechanical modulation means is shown in FIG. 11.

Figures 11, 12:
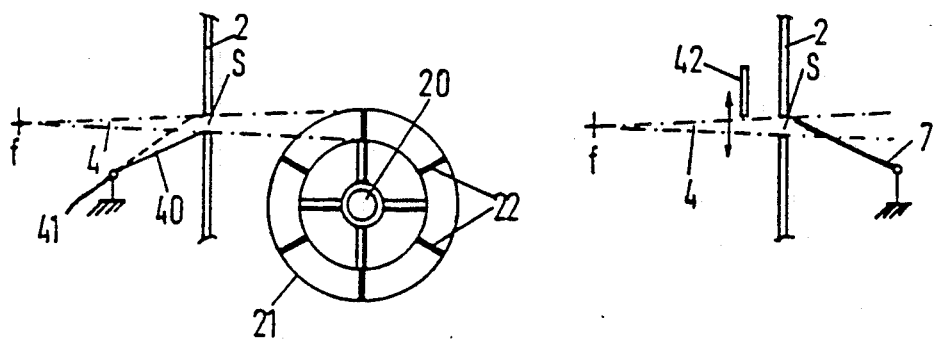

In the embodiment of FIG. 11, a plate-type element 40 is placed between the X-ray source, of which only the X-ray focus f is shown, and the slit diaphragm 2. The plate-type element 40 extends over the entire length of the slit 2 and is drawn in the position exposing the slit completely. A position of the element 40 covering the slit is drawn by means of broken lines. The plate-type element can swing or rotate with respect to one longitudinal edge 41 thereof. It is possible to cause the plate-type element to swing backwards and forwards cyclically between the two positions drawn, but it is equally possible to cause the plate-type element to rotate about the edge 41 or a spindle joined thereto which extends transversely to the plane of the drawing.

In the first case, the plate-type element may advantageously be manufactured from piezoelectric material, the element swinging backwards and forwards between the two positions drawn with respect to the solidly mounted edge under the influence of a cyclic control voltage.

In the second case several plate-type blades extending radially with respect to a rotation spindle may be used so that a similar construction arises to that of the blade wheel described earlier, provided the blades extend over the entire length of the slit and thus influence all the sectors simultaneously and in the same manner. Such a construction could be described as a blade roller.

It is also possible to use a plate-type element which slides up and down in front of the slit S, as shown at 42 in FIG. 12.

Attention is drawn to the fact that the manner of fixed modulation of the X-ray beam 4 is independent of the chosen embodiment of the attenuation elements operating in each sector. In FIG. 11, the attenuation elements are shown by way of example as blade wheels, while in FIG. 12 the attenuation elements are tongue-shaped.

Attention is moreover drawn to the fact that the mechanical modulation means may optionally be situated in front of or behind the slit. This also applies to the attenuation elements, so that the mechanical modulation means and the attenuation elements may be interchanged in position with respect to the embodiment shown in FIGS. 11 and 12, or they may be situated on the same side of the slit. This also applies to the embodiments still to be described below.

Figure 13:
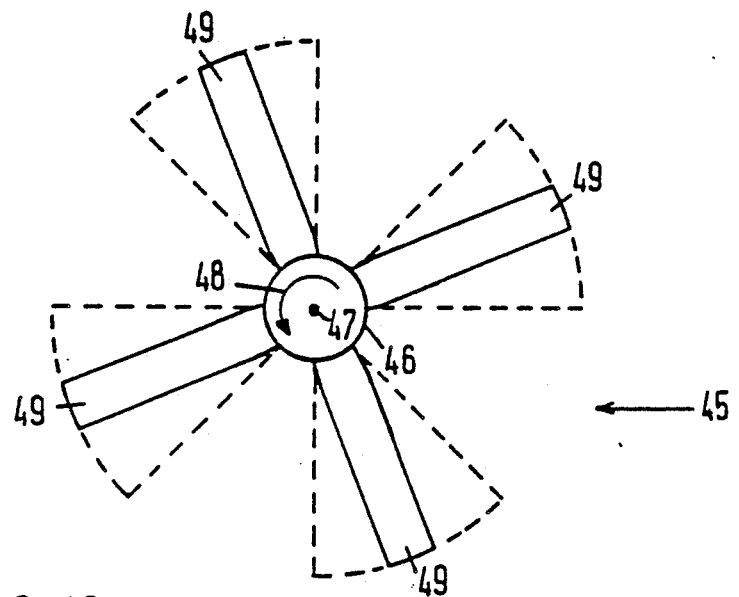
Figure 14:
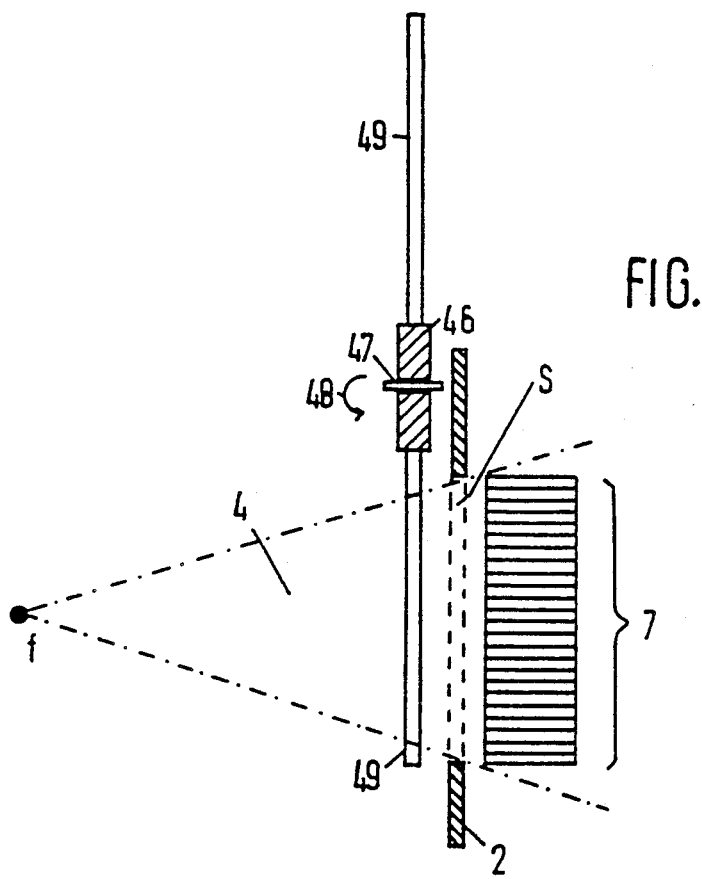

FIGS. 13 and 14 illustrate an alternative embodiment of mechanical modulation means which can be used in a system according to the invention. FIG. 13 shows a segment wheel 45 constructed from a central hub 46, which can rotate around a spindle 47 as indicated by an arrow 48. The hub is provided with a number of radial arms 49 made of material which attenuates X-ray radiation. In the example shown, four arms 49 are used, but it is also possible to use more or fewer arms. In principle one arm can suffice.. The segment wheel is set up in a manner such that in operation, the arms rotate along the slit S. For this purpose, as shown in FIG. 14, the spindle 47 extends transversely to the plane of the slit diaphragm 2.

Figure 15:
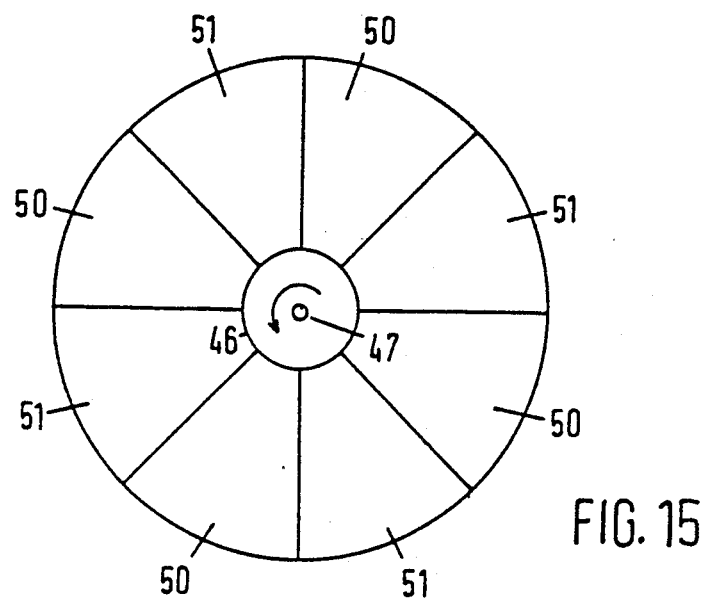

FIG. 14 shows a device according to the invention provided with such a segment wheel in plan view. The space between the arms which attenuate X-ray radiation may be filled in with material transparent to X-ray radiation in order to give the segment wheel more rigidity, but it may also be open. In order to make the effect of the arms rotating along the slit S the same over the entire length of the slit, the arms may advantageously be constructed in segment form, as indicated by broken lines in FIG. 13. A segment wheel as described above may also be constructed with consecutive segments of two materials which both affect the X-ray beam but in different manners. An example is shown in FIG. 15. The segments 50 may, for example, consist of lead and the intervening sectors 51, for example, of copper. Other material combinations may also be used, such as, for example, aluminium and copper or lead and aluminium.

It is possible to use a segment wheel in combination with fixed beam modulation obtained by varying the high voltage of the X-ray tube. If the X-ray beam contains both hard and soft radiation, this offers the possibility of filtering out the soft radiation during the peaks of the varying high voltage (FIG. 2) by using a segment wheel, the arms of which situated at said instants in front of the slit blocking the soft X-ray radiation.

If a blade roller is used, a similar effect can be achieved by manufacturing the blades alternately of different materials.

Attention is drawn to the fact that in FIG. 14 the attenuation elements 7 are indicated as straight tongues which extend parallel to each other. The tongues may, however, also be placed in a fan-type configuration with a convergence point situated in or near the X-ray focus. In addition, the tongues may be constructed in a conically tapering manner in such a fan-type configuration. In addition, several sets of tongues may be used which are placed, for example, behind each other and/or partially above each other.

Finally, attention is drawn to the fact that, apart from the preceding modifications, various modifications are obvious to those skilled in the art. Thus, for example, the X-ray diaphragm could itself have a mobile longitudinal edge which is cyclically moved towards the other longitudinal edge or away therefrom in order to modulate the X-ray beam.

It is also possible to carry out the common fixed cyclic modulation in accordance with a characteristic other than shown in FIGS. 2 and 4 to 6 incl. FIG. 16 shows, by way of example, a modulation M obtained by half-wave rectification of the sinusoidal high voltage of the X-ray tube, and FIG. 17 shows a variant thereof. FIG. 16 also shows a variant of the manner of control of the beam sector modulators indicated for a single beam sector modulator. According to this variant, the beam sector modulators are controlled at a higher frequency than the common modulation frequency. The amplitude and/or phase of the beam sector modulators can also then be controlled again in the manner already described. If the effect of the specific control signals operating for each sector are left out of consideration, the open and closed phases are equally long in the embodiments shown hitherto. However, this is not necessary. The closed phase could, for example, also be longer than the open phase or vice versa.

FIG. 17 illustrates yet another variant of the basic control of the beam sector modulators which may be used, for example, if the beam sector modulators consist of tongue-shaped attenuation elements. According to FIG. 17, the tongues are made to vibrate rapidly and are then brought already vibrating to the open or closed position. As a result of this, the influence of any hysteresis present in the position of the tongue-shaped attenuation elements can be reduced.

In addition, in all the situations described, it is possible to use data on the transmission of the body to be investigated already stored in a (computer) memory as a basis. These data may be obtained in earlier investigations of the same body. The control signals for the beam sector modulators can then be generated directly on the basis of said data without use having to be made of a detector such as the dosimeter 8.

Such modifications are considered to fall within the scope of the invention.

What is claimed is:

1. Method for slit radiography using an X-ray source and a slit diaphragm placed in front of the X-ray source to form a fan-shaped X-ray radiation beam for scanning a body to be investigated to form an X-ray shadow image on an X-ray detector placed behind the body, which fan-shaped X-ray radiation beam is formed by number of sectors situated next to each other, and in which transmitted X-ray radiation is controlled instantaneously for each sector during the scanning movement by means of controllable beam sector attenuators acting in conjunction with the slit diaphragm, characterized by cyclically modulating said X-ray radiation beam in a predetermined manner for all the sectors simultaneously and individually controlling said controllable beam sector attenuators to control cyclically X-ray beam radiation in each sector in synchronization with the predetermined cyclic modulation of X-ray radiation beam.

2. Method according to claim 1, characterized in that the cyclic control is effected by varying the position of the beam sector attenuators with a fixed cycle between a first position essentially transmitting the X-ray beam and a second variable position.

3. Method according to claim 1, characterized in that the cyclic control is effected by varying the position of the beam sector attenuators between a first position essentially transmitting the X-ray beam and a second position controlling the X-ray beam in a maximum manner, a phase of occurrence of the second position being varied with respect to a common predetermined cyclic modulation.

4. Method according to claim 3, characterized in that a starting point of time of the first position is varied.

5. Method according to claim 3, characterized in that an end point of time of the first position is varied.

6. Method according to claim 3, characterized in that duration of the first position is varied.

7. Method according to claim 1, characterized in that cyclic control is effected by vibrating at varied phase said beam sector attenuators 8. Method according to claim 1, characterized in that cyclic control is effected by vibrations at varied amplitude said beam sector attenuators.

9. Method according to claim 1, characterized in that cyclic control is effected at varied phase and amplitude said beam sector attenuators.

10. Method according to one of the preceding claims, characterized in that for each sector signals are generated which are representative of the transmission of the body to be investigated and in that each controllable beam sector attenuators is controlled in accordance with the associated signal.

11. Method according to claim 7 characterized in that a faster second vibration is superimposed on an initial vibration.

12. Method according to claim 8 characterized in that a faster second vibration is superimposed on an initial vibration.

13. Method according to claim 9 characterized in that a faster second vibration is superimposed on an initial vibration.

14. A device for slit radiography comprising an X-ray source, a slit diaphragm placed in front of the X-ray source which forms a fan-shaped X-ray beam with which a body to be investigated can be scanned at least partially to form an X-ray shadow image of the scanned part of the body on an X-ray detector placed behing the body, a control signal generator which, during operation, provides a signal representing the transmission of the body for each sector of the X-ray beam to control means, controllable beam sector attenuators which act in conjunction with the slit diaphragm and which, under the control of the signals from the control means, are able to control the X-ray beam for each sector, characterized by means for providing an X-ray beam modulation for all sectors simultaneously and in a predetermined cyclic manner, said beam sector attenuators being controlled individually in synchronism with cyclic modulation of X-ray radiation.

15. A device according to claim 14, characterized in that the control means control the beam sector attenuators in a manner such that the beam sector attenuators are each brough to an open position, in which the X-ray radiation is able to pass the beam sector attenuators, during at least a part of a first time interval in a rhythm synchronized with the modulation of the X-ray beam, and can be brought to a closed position, in which the beam sector attenuators control the X-ray beam in a maximum manner, during at least a part of a second time interval situated between two first time intervals, and in that the control means are constructed to receive input signals from a radiation detector, which input signals represent quantity of radiation transmitted by the body during at least one measurement interval coinciding at least partially in each case with a first time interval, and if the quantity of radiation in a sector measured during a measurement interval is less than a predetermined value, the control means deliver a control signal which has the effect that the beam sector attenuator associated with said sector is not brought to the closed position during a second time interval following the measurement interval.

16. A device according to claim 15, characterized in that the control means delivers, if the quantity of radiation transmitted by the body during a measurement interval in a sector is less than the predetermined value, a signal which keeps the beam sector attenuator associated with said sector in open position during a subsequent second time interval.

17. A device according to claim 16, characterized in that the control means delivers, if the quantity of radiation measured during a measurement interval in a sector is between two predetermined values, a control signal which brings the beam sector attenuator associated with said sector to a predetermined intermediate position situated between open and closed position.

18. According to claim 14, characterized in that the control means control the beam sector attenuators in a manner such that the beam sector attenuators are each brough to the open position, in which the X-ray beam is able to pass the beam sector attenuators, in a rhythm synchronized with the modulation of the X-ray beam during at least a part of first time interval, and are brought to closed position in which the beam sector attenuators control the X-ray beam in a maximum manner during at least a part of the second time interval which are each situated between two first time intervals, and in that control means receive input signals from the radiation detector, which input signals represent the quantity of radiation transmitted by the body during a measurement interval coinciding each case at least partially with a first time interval, the control means delivering control signals which correspond to the input signals and which control the phase of a subsequent open position interval with respect to cyclic modulation.

19. A device according to claim 18, characterized in that the control signals control length of a subsequent open position interval.

20. A device according to claim 14, characterized in that the modulation means modulates amplitude of supply voltage of the X-ray tube of the X-ray source.

21. A device according to claim 14, characterized in that the modulation means modulates amplidude of current flowing through the X-ray tube of the X-ray source.

22. A device according to claim 14, characterized in that the modulation means comprises at least one element which attenuates X-ray radiation and which cyclically covers or exposes the slit of the slit diaphragm.

23. A device according to claim 22, characterized in that the modulation means comprises a plate-type element extending essentially parallel to a longitudinal direction of the slit of the slit diaphragm over the full length of the slit and at least partially cyclically into a position covering the slit.

24. A device according to claim 22, characterized in that the plate-type element is mounted in a pivotable manner with respect to a spindle situated outside the X-ray beam and extending essentially parallel to said longitudinal direction of the slit.

25. A device according to claim 23, characterized in that the plate-type element is manufactured from piezoelectric material and can swivel into the X-ray beam under the influence of electrical signals with respect to a longitudinal edge, mounted in a fixed manner by means of the other longitudinal edge.

26. A device according to claim 22, characterized in that the modulation means comprise a roller which can be rotated about a spindle extending essentially parallel to the longitudinal direction of the slit, said roller being provided with a number of radial blades of material which attenuates X-ray radiation and extend over a full length of the slit.

27. According to claim 26, characterized in that the radial blades are manufactured of materials which influence X-ray radiation in different manners.

28. A device according to claim 22, characterized in that the modulation means comprise a segmented wheel rotated about a spindle extending transversely with respect to a plane containing the slit of the slit diaphragm located laterally next to the slit said segmented while having a radius at least as large as the length of the slit and having at least one segment manufactured from material attenuating X-ray radiation.

29. A device according to claim 28, characterized in that the segmented wheel comprises a hub provided with a number of radial arms of material attenuating X-ray radiation.

30. A device according to claim 28, characterized in that the segmented wheel comprises first and second segments which alternate with each other and which are manufactured from a first or second material influencing X-ray radiation in different manners.

31. A device according to claim 29, characterized in that the first material transmits soft X-ray radiation and in that the second material transmits essentially hard X-ray radiation.

32. A device according to claim 30, characterized in that said first and second segments are manufactured from lead and copper, respectively.

33. A device according to claim 30, characterized in that said first and second segments are manufactured from aluminum and copper, respectively.

34. A device according to claim 30, characterized in that said first and second segments are manufactured alternately from lead and aluminum, respectively.

35. A device according to claim 14, characterized in that the controllable beam sector attenuators comprise a blade disc, each blade disc comprising at least one blade of material attenuating X-ray radiation, said blade discs being mounted next to each other on a rotable spindle extending essentially parallel to a longitudinal direction of the slit of the slit diaphragm, said blade discs being variably positionable with respect to said rotatable spindle.

36. A device according to claim 35, characterized in that each blade disc is mounted in a slipping manner on the spindle.

37. A device according to claim 35, characterized in that each blade disc is mounted in a sprung manner on the spindle.

38. A device according to claim 35, characterized in that each blade disc is provided with a brake element energized by the control means and by means of which the position of the associated blade disc can be changed with respect to the spindle.

39. A device according to claim 38, characterized in that the blade discs have a circumferential face with which a brake block.

40. A device according to claim 38, characterized in that the brake element is an eddy-current brake.

* * * * *